(12) United States Patent (10) Patent No.: US 7,517,596 B2
Igawa et al. (45) Date of Patent: Apr. 14, 2009

(54) PHENANTHROLINE COMPOUND AND LIGHT-EMITTING DEVICE

(75) Inventors: Satoshi Igawa, Fujisawa (JP); Shinjiro Okada, Kamakura (JP); Takao Takiguchi, Tokyo (JP); Manabu Furugori, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 374 days.

(21) Appl. No.: 11/272,726

(22) Filed: Nov. 15, 2005

(65) Prior Publication Data

US 2006/0115676 A1 Jun. 1, 2006

(30) Foreign Application Priority Data

Nov. 29, 2004 (JP) ............................. 2004-344041

(51) Int. Cl.
*H01L 51/54* (2006.01)
*C07D 41/00* (2006.01)

(52) U.S. Cl. .................. 428/690; 428/917; 313/504; 546/88; 548/440

(58) Field of Classification Search ................ 428/690, 428/917; 313/504, 506; 257/E51.044, 102, 257/103; 546/88, 440
See application file for complete search history.

(56) References Cited

U.S. PATENT DOCUMENTS 5,393,614 A 2/1995 Nakada ...................... 428/690

(Continued)

FOREIGN PATENT DOCUMENTS

CN 1477175 * 2/2004

(Continued)

OTHER PUBLICATIONS

Guan et al., New Journal of Chemistry, vol. 27, pp. 1731-1734.*

(Continued)

*Primary Examiner*—Dawn Garrett
(74) *Attorney, Agent, or Firm*—Fitzpatrick, Cella, Harper & Scinto (57) ABSTRACT

A novel phenanthroline compound is provided which is suitable as a compound for an organic EL device and is represented by the general formula (I):

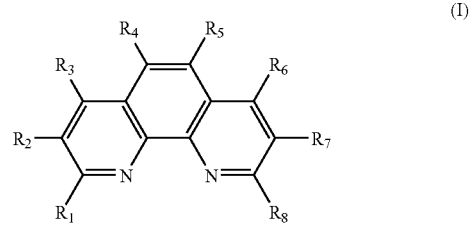

wherein $R_1$, $R_2$, $R_3$, $R_4$, $R_5$, $R_6$, $R_7$, and $R_8$ are each independently a hydrogen atom, an alkyl group, a substituted or unsubstituted aralkyl group, a substituted or unsubstituted aryl group, a substituted or unsubstituted heterocyclic group, or a halogen atom with the proviso that at least one of $R_1$, $R_2$, $R_3$, $R_4$, $R_5$, $R_6$, $R_7$, and $R_8$ is a group represented by the general formula (II):

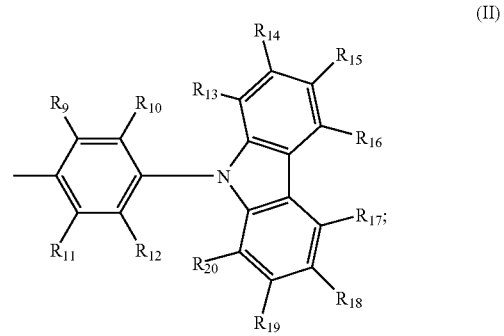

and $R_9$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ are each independently a hydrogen atom, an alkyl group, a substituted or unsubstituted aryl group, a substituted or unsubstituted heterocyclic group, or a halogen atom.

8 Claims, 1 Drawing Sheet

U.S. PATENT DOCUMENTS

| 6,812,497 | B2 | 11/2004 | Kamatani et al. | 257/79 |
| 6,972,334 | B1 | 12/2005 | Shibanuma et al. | 546/88 |
| 2006/0097227 | A1 | 5/2006 | Okajima et al. | |

FOREIGN PATENT DOCUMENTS

| JP | 05-331459 | | 12/1993 |
| JP | 2001-131174 | | 5/2001 |
| JP | 2001-267080 | | 9/2001 |
| JP | 2004-071380 | * | 3/2004 |
| JP | 2004-107263 | * | 4/2004 |
| WO | WO 2004/026870 | * | 4/2004 |
| WO | WO 2004/026870 A1 | * | 4/2004 |

OTHER PUBLICATIONS

JPO machine translation for JP 2004-071380 published Mar. 2004.*
Journal of the American Chemical Society, (2003), vol. 125, No. 18, p. 5356-5365.*

F.H. Case; "Substitutional 1,10 Phenanthrolines.IV.Bromo Derivatives"; J. Org. Chem., vol. 16, 941-945 (1951).
Tzalis et al.; "Simple One-Step Synthesis . . . Metal Chelates"; Tetrahedron Letters; vol. 36, No. 20, 3489-3490 (1995).
Vincett et al.; "Electrical Conduction . . . Vacuum Deposited Organic Films"; Thin Solid Films, vol. 94, 171-183 (1982).
Burroughes et al.; Light-emitting diodes based in conjugated polymers; Nature, vol. 347, 539-541 (1990).
Miyaura et al.; "Palladium-Catalyzed . . . Organoboron Compounds"; Chem. Rev., vol. 95, 2457-2483 (1995).
Chen et al.; Recent Developments in . . . Electroluminescent Materials; Macromol. Symp., vol. 125, 1-48 (1997).
O'Brien et al.; "Improved energy transfer in electrophosphorescent devices"; Appl. Phys. Lett., vol. 74, No. 3, 442-444 (1999).
Baldo, et al.; "Very high-efficiency green . . . in electrophosphorescence"; Appl. Phys. Lett., vol. 75, No. 1, 4-6 (1999).

* cited by examiner

PHENANTHROLINE COMPOUND AND LIGHT-EMITTING DEVICE

BACKGROUND OF THE INVENTION

1. Field of the Invention

The present invention relates to a phenanthroline compound and a light-emitting device using the compound. More specifically, the present invention relates to a phenanthroline compound having a molecular structure represented by the following general formula (I) and an organic electroluminescent (EL) device using the compound for a host of a light-emitting layer.

2. Related Background Art

In an old example of an organic light-emitting device, a voltage has been applied to an anthracene evaporated film to emit light (Thin Solid Films, 94 (1982), 171). However, because of ease of large-area production compared with inorganic light-emitting devices, obtainability of desired color emission by the development of various new materials, and low voltage drivability, in recent years, active research including material development is being conducted for the development of an organic light-emitting device as a light-emitting device having high-speed responsibility and high efficiency.

For example, as detailed in Macromol. Symp. 125, 1-48 (1997), an organic EL device is generally structured to have two (upper and lower) electrodes formed on a transparent substrate and an organic substance layer including a light-emitting layer formed between the electrodes. In addition, investigation has been recently made into a device using not only conventional light emission utilizing fluorescence upon transition from singlet exciton to ground state but also phosphorescence via triplet exciton as typified by D. F. O'Brien et al, "Improved energy transfer in electrophosphorescent device", Applied Physics Letters, Vol. 74, No. 3, p. 422 (1999) and M. A. Baldo et al, "Very high-efficiency green organic light-emitting devices based on electrophosphorescence", Applied Physics Letters, Vol. 75, No. 1, p. 4 (1999). In these articles, an organic layer having a four-layer structure is mainly used. The structure is composed of a hole-transporting layer, a light-emitting layer, an exciton diffusion-prevention layer, and an electron-transporting layer stacked in the mentioned order from an anode side. The materials used are carrier transporting materials and a phosphorescent material Ir(ppy)$_3$ shown below.

Further, emission of a light from ultraviolet to infrared region can be performed by changing the kind of a fluorescent organic compound. In these days, research has been actively conducted on various compounds.

In addition to organic light-emitting devices using such low-molecular materials as those described above, a group of the University of Cambridge has reported organic light-emitting devices using conjugate polymers (Nature, 347, 539 (1990)). This report has confirmed that light emission can be obtained by a single layer by forming polyphenylene vinylene (PPV) in a film shape by use of a coating system.

As described above, recent progress of an organic light-emitting device is remarkable, and is characterized in that a highly responsive, thin, and lightweight light-emitting device that can be driven at a low applied voltage and provides a high luminance and a variety of emission wavelengths can be made, which suggests the applicability to a wide variety of uses.

However, at present, an optical output of a higher luminance and a higher conversion efficiency have been required. In addition, there still remain a large number of problems in terms of durability such as a change over time during long-term use and degradation due to an atmospheric gas containing oxygen or to moisture. Furthermore, light emission of blue, green and red colors having a high color purity is necessary when application to a full-color display or the like is attempted. However, those problems have not been sufficiently solved yet.

In addition, a large number of aromatic compounds and condensed polycyclic aromatic compounds have been studied as fluorescent organic compounds used for an electron-transporting layer, a light-emitting layer, and the like. However, it is difficult to say that a compound sufficiently satisfying the emission luminance and durability requirements has been already obtained.

Examples of patent documents describing application of a phenanthroline compound to an organic EL, which is related to the present invention, include Japanese Patent Application Laid-Open Nos. H05-331459, 2001-267080 and 2001-131174. However, none of these patent documents discloses an organic compound in accordance with the present invention characterized by including a partial structure containing a fluorene ring and a phenyl ring on a straight line in a molecular structure.

In order to apply an organic EL device to a display unit of a display apparatus or the like, the device is required to have an optical output of a high efficiency and a high luminance and sufficiently secure high durability. However, such requirement has not been sufficiently met.

DISCLOSURE OF THE INVENTION

It is, therefore, an object of the present invention to provide a novel phenanthroline compound that can be suitably used as a compound for an organic EL device and an organic EL device using the compound and having an optical output of a high efficiency and a high luminance.

It is another object of the present invention to provide an organic EL device with high durability.

It is still another object of the present invention to provide an organic EL device that can be produced easily at a relatively low cost.

According to a first aspect of the present invention, there is provided a phenanthroline compound represented by the following general formula (I):

(I)

wherein $R_1$, $R_2$, $R_3$, $R_4$, $R_5$, $R_6$, $R_7$, and $R_8$ are each independently a hydrogen atom, an alkyl group, a substituted or unsubstituted aralkyl group, a substituted or unsubstituted aryl group, a substituted or unsubstituted heterocyclic group, or a halogen atom with the proviso that at least one of $R_1$, $R_2$, $R_3$, $R_4$, $R_5$, $R_6$, $R_7$, and $R_8$ is a group represented by the following general formula (II):

(II)

and $R_9$, $R_{10}$, $R_{11}$, $R_{21}$, $R_{13}$, $R_{14}$, $R_{15}$, $R_{16}$, $R_{17}$, $R_{18}$, $R_{19}$, and $R_{20}$ are each independently a hydrogen atom, an alkyl group, a substituted or unsubstituted aryl group, a substituted or unsubstituted heterocyclic group, or a halogen atom.

According to another aspect of the present invention, there is provided a light-emitting device comprising a pair of electrodes, and at least one layer comprising an organic compound provided between the pair of electrodes, wherein at least one of the at least one layer comprising the organic compound comprises the phenanthroline compound represented by the general formula (I).

The phenanthroline compound in accordance with the present invention has a high glass transition temperature, and the light-emitting device in accordance with the present invention using the compound, especially for a host of a light-emitting layer, is expected to not only emit light at a high efficiency but also be driven at a low voltage.

DESCRIPTION OF THE PREFERRED EMBODIMENTS

First, the phenanthroline compound in accordance with the present invention will be described.

Specific examples of the substituents in the general formula (I) are shown below.

Examples of the alkyl group include methyl group, ethyl group, n-propyl group, iso-propyl group, n-butyl group, ter-butyl group, and octyl group.

Examples of the aralkyl group include benzyl group and phenethyl group.

Examples of the aryl group include phenyl group, biphenyl group, and terphenyl group.

Examples of the heterocyclic group include thienyl group, pyrolyl group, pyridyl group, oxazolyl group, oxadiazolyl group, thiazolyl group, thiadiazolyl group, and terphenyl group.

Examples of the substituents by which the above-mentioned substituents may be substituted include: alkyl groups such as methyl group, ethyl group, and propyl group; aralkyl groups such as benzyl group and phenethyl group; aryl groups such as phenyl group and biphenyl group; heterocyclic groups such as thienyl group, pyrolyl group, and pyridyl group; amino groups such as dimethylamino group, diethylamino group, dibenzylamino group, diphenylamino group, ditolylamino group, and dianisoylamino group; alkoxyl groups such as methoxyl group, ethoxyl group, propoxyl group, and phenoxyl group; and cyano group; halogen atoms such as fluorine, chlorine, bromine, and iodine.

Specific structural formulae of organic compounds to be used in the present invention are shown below. However, these formulae are shown only by way of examples and are not intended to limit the scope of the present invention.

H-1

H-2

H-3

H-4

H-5

H-6

H-7

H-8

H-9

H-10

H-11

H-12

H-13

H-14    H-15

-continued

H-16

H-17

H-18

H-19

H-20

H-21

H-22

The phenanthroline compound in accordance with the present invention can be synthesized by means of a generally known method. For example, a phenanthroline compound intermediate is obtained by means of a method described in J. Org. Chem., 16, 941-945 (1951), Tetrahedron, Lett., 36, 3489-3490 (1995), or the like, and the compound is synthesized from the intermediate by means of a synthesis method such as the Suzuki coupling method (for example, Chem. Rev. 1995, 95, 2457-2483) involving the use of a palladium catalyst.

Next, the light-emitting device of the present invention will be described.

When a light-emitting layer comprises a carrier transporting host material and a guest, the process for light emission is composed of the following several steps.

1. Transportation of electrons/holes in the light-emitting layer
2. Generation of excitons in the host
3. Transmission of excitation energy between host molecules
4. Transfer of the excitation energy from the host to the guest The desired energy transfer and light emission in the respective steps are caused in competition with various deactivation steps.

It is needless to say that in order to increase the emission efficiency of an EL device, the emission quantum yield of a luminescent center material itself must be large. However, how high efficiency of energy transfer between hosts or between a host and a guest can be achieved is also a large problem. In addition, the cause for degradation of light emission due to energization has not been clarified yet. However, it is assumed that the degradation is related at least to a luminescent center material itself or an environmental change of a light-emitting material due to surrounding molecules.

In view of the above, the inventors of the present invention have made various studies to find that a device using the phenanthroline compound represented by the general formula (1) as a host of a light-emitting layer emits light with a high efficiency, maintains a high luminance for a long period of time, and shows less degradation due to energization.

One possible cause for the degradation of light emission due to energization is degradation of light emission due to degradation of a thin-film shape of a light-emitting layer. It is believed that the degradation of the thin-film shape results from crystallization of an organic thin film due to a temperature of drive environment or heat generation at the time of driving a device. This is considered to originate from a low glass transition temperature of a material, so that an organic EL material is required to have a high glass transition temperature. The phenanthroline compound in accordance with the present invention has a high glass transition temperature, so that the durability of an organic EL device is expected to increase.

Further, in order to obtain a device capable of emitting light with a high efficiency, the drive voltage needs to be lowered. To this end, it is important that a host has charge conductivity. The phenanthroline compound in accordance with the present invention is believed to have a high electron-transporting property, so that low voltage drivability and high emission efficiency can be expected. Moreover, it is preferable from the viewpoint of charge conductivity that the substituents $R_1$ to $R_{20}$ is each independently a hydrogen atom, methyl group, or aryl group.

When the phenanthroline compound in accordance with the present invention is used for a host of a light-emitting layer, there may be used, as a guest molecule, any generally known fluorescent material and phosphorescent material. In order to obtain a light-emitting device having a high efficiency, it is preferable to use a metal coordination compound known to emit phosphorescence such as an Ir complex, a Pt complex, a Re complex, a Cu complex, a Eu complex, or a Rh complex. The Ir complex known to emit strong phosphorescence is more preferable. Further, plural kinds of phosphorescent materials may be incorporated into a light-emitting layer for the purposes of causing the light-emitting layer to effect light emission of multiple colors and aiding excitons or charge transfer.

When an organic layer containing the phenanthroline compound of the present invention is produced, a vacuum evaporation method, a casting method, an application method, a spin coating method, an ink jet method, or the like may be employed.

Figure 1A:
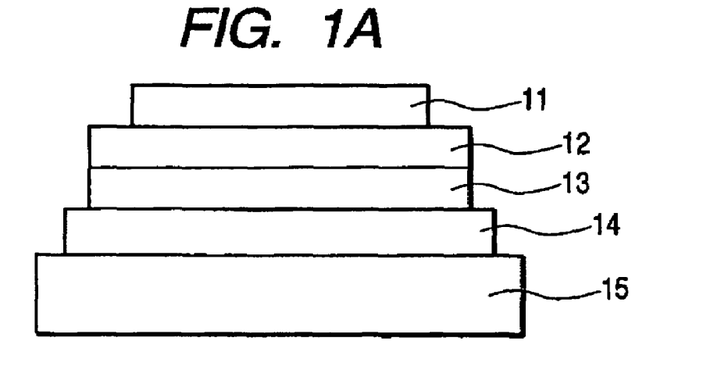
FIGS. 1A, 1B and 1C are schematic views each showing an example of the light-emitting device in accordance with the present invention.
Figure 1B:
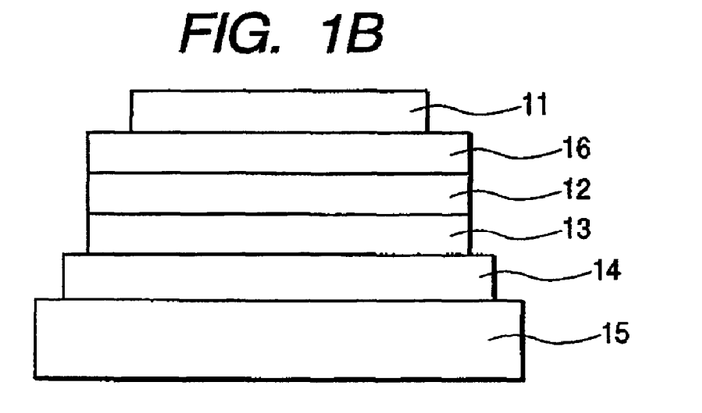
Figure 1C:
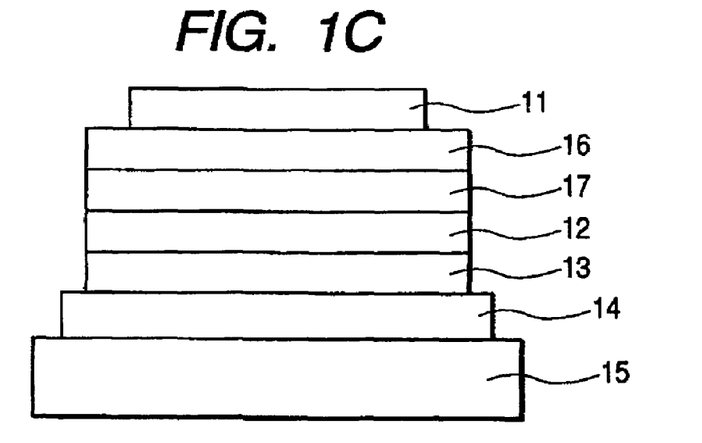

FIGS. 1A, 1B and 1C are schematic views showing basic structures of the device in accordance with the present invention.

As shown in FIGS. 1A, 1B and 1C, an organic EL device generally includes a transparent substrate 15; a transparent electrode 14 having a thickness of 50 to 200 nm on the transparent substrate 15; a plurality of organic film layers on the transparent electrode 14; and a metal electrode 11 to sandwich the plurality of organic film layers between the transparent electrode 14 and the metal electrode 11.

FIG. 1A shows an example in which the organic layers are composed of a light-emitting layer 12 and a hole-transporting layer 13. As the transparent electrode 14, ITO having a large work function is used, so that holes can be easily injected from the transparent electrode 14 to the hole-transporting layer 13. For the metal electrode 11, a metal material having a small work function such as aluminum, magnesium, or an alloy thereof is used, so that electrons can be easily injected to the organic layers.

For the light-emitting layer 12, the compound in accordance with the present invention is preferably used. For the hole-transporting layer 13, there may be used those materials having electron-donating property, for example, a triphenyldiamine derivative typified by α-NPD.

The device having the structure described above exhibits electric rectification property. When an electric field is applied thereto with the metal electrode 11 being used as a cathode and the transparent electrode 14 being used as an anode, electrons are injected from the metal electrode 11 to the light-emitting layer 12, while holes are injected from the transparent electrode 14.

The injected holes and electrons are recombined in the light-emitting layer 12 to generate excitons, thereby effecting light emission. At this time, the hole-transporting layer 13 serves as an electron blocking layer, so that the recombination efficiency at an interface between the light-emitting layer 12 and the hole-transporting layer 13 increases to thereby increase the emission efficiency.

In FIG. 1B, an electron-transporting layer 16 is further provided between the metal electrode 11 and the light-emitting layer 12 of the device shown in FIG. 1A. A light-emitting function and electron/hole transporting functions are separated in this manner to attain a more effective carrier blocking structure, whereby the emission efficiency is increased. For the electron-transporting layer 16, there may be used, for example, an oxadiazole derivative or the like.

Further, as shown in FIG. 1C, a four-layer structure may preferably be adopted which is composed of the hole-transporting layer 13, the light-emitting layer 12, an exciton diffusion-prevention layer 17, and the electron-transporting layer 16 stacked in the mentioned order from the side of the transparent electrode 14 as the anode, and the metal electrode 11 further stacked thereon.

EXAMPLES

Hereinafter, the present invention will be described specifically by way of examples. However, the present invention is not limited to these examples.

Example 1

Synthesis of Exemplified Compound No. H-6

1.5 g (4.4 mmole) of 2,9-dibromophenanthroline, 2.55 g (8.9 mmole) of 4-(9H-carbazoyl-9-yl)phenylboronic acid, 0.15 g of Pd(PPh$_3$)$_4$, 20 ml of toluene, 10 ml of ethanol, and 20 ml of a 2M aqueous solution of sodium carbonate were fed into a reaction vessel, and the whole was stirred at 80° C. for 8 hours in a stream of nitrogen. After the completion of the reaction, the crystal was filtered out and washed with water, ethanol, and toluene. The resulting crystal was dissolved into chloroform, purified by means of alumina column chromatography, then vacuum-dried at 120° C., and sublimated and purified to give 1.5 g of Exemplified Compound No. H-6 (yield: 50.8%).

662.3 as M+ of the compound was confirmed by means of Matrix Assisted Laser Desorption/Ionization-Time of Flight Mass Spectrometry (MALDI-TOF MS).

Furthermore, the structure of the compound was identified by NMR measurement.

$^1$H NMR (CDCl$_3$, 400 MHz) σ (ppm): 9.59 (d, 2H), 8.55 (d, 2H), 8.18 (d, 4H), 8.05 (d, 4H), 7.99 (s, 2H), 7.80 (d, 4H), 7.53 (d, 4H), 7.46 (m, 4H), 7.34 (m, 4H)

Moreover, the compound had a glass transition temperature of 166° C.

Example 2

In this example, a device having three organic layers shown in FIG. 1B was used as a device structure.

ITO (as the transparent electrode 14) having a thickness of 100 nm was patterned on a glass substrate (as the transparent substrate 15). The following organic layers and electrode layers were successively formed on the ITO substrate by means of vacuum evaporation according to resistive heating in a vacuum chamber having an internal pressure of 10$^{-5}$ Pa such that the opposing electrode area was 3 mm$^2$.

Hole-transporting layer 13 (20 nm): α-NPD

Light-emitting layer 12 (25 nm): [Host] Exemplified Compound No. H-6, [Guest] Ir(piq)$_3$ (weight ratio: 10%)

Electron-transporting layer 16 (50 nm): Bphen (manufactured by DOJINDO LABORATORIES)

Metal electrode layer 11-1 (1 nm): KF

Metal electrode layer 11-2 (100 nm): Al

Ir(piq)3

The current-voltage characteristics of the EL device were measured by using a microammeter 4140B (manufactured by Hewlett-Packard Development Company), and the emission luminance thereof was measured by using a BM7 (manufactured by Topcon Corporation).

The device of this example had a current efficiency and a power efficiency of 9.1 cd/A and 10.0 lm/W (at 600 cd/m$^2$), respectively. Further, the applied voltage at the time of light emission of 1,000 cd/m$^2$ was 3.2 V. The results are shown in Table 1 below.

Comparative Example 1

A device was produced by following the same procedure as in Example 2 with the exception that CBP shown below was used instead of Exemplified Compound No. H-6 of Example 2.

CBP

The device of this comparative example had a current efficiency and a power efficiency of 8.0 cd/A and 6.0 lm/W (at 600 cd/m$^2$), respectively. Further, the applied voltage at the time of light emission of 1,000 cd/m$^2$ was 4.5 V. The results are shown in Table 1 below.

TABLE 1

| | Host compound | Efficiency (lm/W) at 600 cd/m$^2$ | Voltage (V) at 1,000 cd/m$^2$ |
|---|---|---|---|
| Example 2 | H-6 | 10.0 | 3.2 |
| Comparative Example 1 | CBP | 6.0 | 4.5 |

Example 3

Synthesis of Exemplified Compound No. H-7

1.5 g (4.4 mmole) of 3,8-dibromophenanthroline, 2.55 g (8.9 mmole) of 4-(9H-carbazoyl-9-yl)phenylboronic acid, 0.15 g of Pd(PPh$_3$)$_4$, 20 ml of toluene, 10 ml of ethanol, and 20 ml of a 2M aqueous solution of sodium carbonate were fed into a reaction vessel, and the whole was stirred at 80° C. for 8 hours in a stream of nitrogen. After the completion of the reaction, the crystal was filtered out and washed with water, ethanol, and toluene. The resultant crystal was dissolved into chloroform, purified by means of alumina chromatography, and then vacuum-dried at 120° C., and sublimated and purified to give 1.6 g of Exemplified Compound No. H-7 (yield: 54.2%).

662.3 as M+ of the compound was confirmed by means of Matrix Assisted Laser Desorption/Ionization-Time of Flight Mass Spectrometry (MALDI-TOF MS).

Furthermore, the structure of the compound was identified by NMR measurement.

$^1$H NMR (CDCl$_3$, 400 MHz) σ (ppm): 8.70 (d, 4H), 8.42 (d, 2H), 8.27 (d, 2H), 8.15 (d, 4H), 7.88 (s, 2H), 7.81 (d, 4H), 7.54 (d, 4H), 7.43 (m, 4H), 7.29 (m, 4H)

Moreover, the compound had a glass transition temperature of 168° C.

Example 4

A device was produced by following the same procedure as in Example 2 with the exception that Exemplified Compound No. H-7 was used instead of Exemplified Compound No. H-6 of Example 2; and Ir(4mopiq)$_3$ (weight ratio: 4%) and Ir(bq)$_3$ (weight ratio: 8%) were used instead of Ir(piq)$_3$ (weight ratio: 10%), and was subjected to similar measurement.

Ir(4mopiq)3

Ir(bq)3

The device of this example had a current efficiency and a power efficiency of 17.5 cd/A and 16.7 lm/W (at 600 cd/m$^2$), respectively. Further, the applied voltage at the time of light emission of 1,000 cd/m$^2$ was 3.5 V. The results are shown in Table 2 below.

Comparative Example 2

A device was produced by following the same procedure as in Example 4 with the exception that CBP was used instead of Exemplified Compound No. H-7 of Example 4, and was subjected to similar measurement.

The device of this comparative example had a current efficiency and a power efficiency of 17.0 cd/A and 12.0 lm/W (at 600 cd/m$^2$), respectively. Further, the applied voltage at the time of light emission of 1,000 cd/m$^2$ was 5.0 V. The results are shown in Table 2 below.

TABLE 2

| | Host compound | Efficiency (lm/W) at 600 cd/m$^2$ | Voltage (V) at 1,000 cd/m$^2$ |
|---|---|---|---|
| Example 4 | H-7 | 16.7 | 3.5 |
| Comparative Example 2 | CBP | 12.0 | 5.0 |

As described in detail above, the device using the phenanthroline compound in accordance with the present invention is an excellent device which can be driven at a low voltage and has a high efficiency.

This application claims priority from Japanese Patent Application No. 2004-344041 filed Nov. 29, 2004, which is hereby incorporated by reference herein.

What is claimed is:

1. A phenanthroline compound represented by the following formula H-6 or formula H-7:

H-6

H-7

2. A light-emitting device comprising a pair of electrodes, and at least one layer comprising an organic compound provided between the pair of electrodes, wherein at least one of the at least one layer comprising the organic compound comprises the phenanthroline compound as set forth in claim 1.

3. The light-emitting device according to claim 2, wherein the layer comprising the phenanthroline compound is a light-emitting layer.

4. The light-emitting device according to claim 3, wherein the light-emitting layer comprises at least two compounds including a host and a guest compounds, and the host compound comprises the phenanthroline compound.

5. The light-emitting device according to claim 4, wherein the guest compound is a phosphorescent material.

6. The light-emitting device according to claim 5, wherein the phosphorescent material comprises a metal coordination compound.

7. The light-emitting device according to claim 6, wherein the metal coordination compound comprises an iridium coordination compound.

8. The light-emitting device according to claim 3, wherein the light-emitting layer comprises a plurality of phosphorescent materials.

* * * * *